United States Patent [19]
Bombardelli et al.

[11] Patent Number: 6,147,082
[45] Date of Patent: Nov. 14, 2000

[54] CHALCONES HAVING ANTIPROLIFERATIVE ACTIVITY

[76] Inventors: Ezio Bombardelli; Piero Valenti, both of c/o Viale Ortles, 12, I-20139, Milan, Italy

[21] Appl. No.: 09/445,179

[22] PCT Filed: Jun. 12, 1998

[86] PCT No.: PCT/EP98/03558

§ 371 Date: Dec. 8, 1999

§ 102(e) Date: Dec. 8, 1999

[87] PCT Pub. No.: WO98/58913

PCT Pub. Date: Dec. 30, 1998

[30] Foreign Application Priority Data

Jun. 19, 1997 [GB] United Kingdom .................. 9712966

[51] Int. Cl.$^7$ ..................... A61K 31/435; A61K 31/44; C07D 211/70; C07D 209/04
[52] U.S. Cl. .................. 514/277; 514/357; 514/415; 546/344; 546/346; 546/348; 548/509
[58] Field of Search ..................... 514/277, 357, 514/415; 546/344, 346, 348; 518/509

[56] References Cited

FOREIGN PATENT DOCUMENTS

WO 91/17749  11/1991  WIPO .
WO 96/19209   6/1996  WIPO .

OTHER PUBLICATIONS

S. Budavari; "The Merck Index, An Encyclopedia of Chemicals, Drugs and Biologicals"; 12$^{th}$ edition; 1996; p. 1381.

T. Konoshima et al.; "Studies on inihibitors of skin tumor promotion (V). Inhibitory effects of flavonoids of Epstein–Barr virus activation II.", Shoyakugaku Zasshi; ISSN 0037–4377, vol. 43, No. 2, 1989, pp. 135–141.

A. Verma et al.; "Inhibition of 7, 12–Dimethylbenz(a)anthracene–and N–Nitrosomethylureau–induced Rat Mammary Cancer by Dietary Flavonol Quercetin"; *Cancer Research*, 1988, vol. 48, pp. 5754–5758.

J. Cassady; "Natural Products as a Source of Potential Cancer Chemotherapeutic and Chemopreventive Agents"; *Journal of Natural Products*, 1990, vol. 53, No. 1, pp. 23–41.

L. M. Larocca et al.; "Type II oestrogen binding sites in acute lymphoid and myeloid leukaemias: growth inhibitory effect of oestrogen and flavonoids"; *British Journal of Haematology*; 1990; 75; pp. 489–495.

G. Scambia et al.; "Inhibitory effect of quercetin on OVCA 433 cells and presence of type II oestrogen binding sites in primary ovarian tumours and cultured cells"; *British Journal Cancer*; 1990; 62; pp. 942–946.

J. Eliason et al.; Human Multi–Drug–Resistant Cancer Cells Exhibit A High Degree of Selectively for Steroisomers of Verapamil and Quinidine; *International Journal Cancer*; 1990; 46, pp. 113–117.

G. Scambia et al.; "Inhibitory Effect of Quercetin on Primary Ovarian and Endometrial Cancers and Synergistic Activity with cis–Diamminedichloroplatinum (II)"; *Gynecologic Oncology*; 1992; 45; pp. 13–19.

*Primary Examiner*—D. Margaret Seaman
*Attorney, Agent, or Firm*—Pennie & Edmonds LLP

[57] ABSTRACT

The invention relates to a novel class of compounds that have structures related to certain naturally occurring or synthetic chalcones. The invention also relates to pharmaceutical compositions comprising the compounds and methods for treating certain disorders using the pharmaceutical compositions. The invention further relates to process for synthesizing the novel class of compounds.

13 Claims, No Drawings

CHALCONES HAVING ANTIPROLIFERATIVE ACTIVITY

FIELD OF THE INVENTION

The present invention relates to a novel class of compounds which have structures related to certain naturally occurring and synthetic chalcones, as well as to methods for the preparation of such compounds and to pharmaceutical uses thereof.

BACKGROUND OF THE INVENTION

The compound 1,3-diphenyl-2-propene-1-one is known by the trivial name "chalcone". Many naturally occurring flavonoids share structural features with chalcone and are referred to by the generic term "chalcones". Also, certain flavonoids, including ones which are also classified as chalcones, have recently been demonstrated to have anti-cancer activity (Cancer Research, 48, 5754, 1988) and chemopreventive activity in some tumours (J. Nat. Prod., 53, 23, 1990).

In particular, quercetin, an ubiquitous flavonoid found in plants, has been shown to act on the proliferation of human leukemic cells (Br. J. of Haematology, 75, 489, 1990) and on other cell lines (Br. J. Cancer, 62, 94, 942, 1990; Int. J. Cancer, 46, 112, 1990; Gynecologic Oncology, 45, 13, 1992) and to possess a synergic action with common antiblastic drugs.

In addition, some natural or synthetic chalcones, described in our International Patent Publication No. WO 91/17749 and in International Patent Publication No. WO 96/19209 (Baylor College of Medicine) have proved to have a significant antiproliferation activity on a variety of different cell lines.

Although the mechanism of action of the antiproliferation activity of flavonoids and chalcones is still unknown, it is believed to be linked to the interaction of these compounds with type II estrogen receptors.

The action in vivo of these polyphenol substances is certainly much more complicated. All these compounds are generally characterized by an almost complete insolubility in water and, in vivo, by a very poor bioavailability linked to a rapid metabolism of phenols and a marked affinity for lipids and proteins.

SUMMARY OF THE INVENTION

Surprisingly, it has now been found that certain novel chalcones, chalcone derivatives and chalcone analogues, in particular ones in which the phenyl ring in the 3-position is substituted or replaced by rings containing one or more heteroatoms, possess a greater antiproliferation activity both on sensitive cancerous cells and on cells which are resistant to common chemotherapeutic drugs, including the latest generation anti-neoplastic agents, paclitaxel and docetaxel.

DETAILED DESCRIPTION OF THE INVENTION

Thus according to one aspect of the present invention, there are provided compounds of the general formula (A)

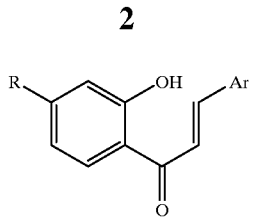

wherein:
Ar represents phenyl, which may be unsubstituted or substituted by one, two or three substituents independently selected from Cl, Br, F, —OMe, $NO_2$, $CF_3$, $C_{1-4}$ lower alkyl (preferably methyl), —$NMe_2$, —$NEt_2$, —$SCH_3$, —$NHCOCH_3$; 2-thienyl; 2-furyl; 3-pyridyl, 4-pyridyl or 3-indolyl;
R represents —$OCH_2R_1$, in which $R_1$ is selected from —CH=$CMe_2$, —CMe=$CH_2$, —C≡CH; with the proviso that where Ar represents phenyl, R is other than 3-methyl-2-butenyl oxy.

Within this class, preferably Ar is selected from unsubstituted phenyl, 3-pyridyl, 4-pyridyl and 3-indolyl. Particularly preferred are compounds wherein R represents —$OCH_2$—CH=$CMe_2$, —$OCH_2$—CMe=$C_2$, or —$OCH_2$—C≡CH.

Compounds of formula (A) which contain a basic amino function may be converted to acid addition salts with pharmaceutically acceptable acids such as hydrochloric and phosphoric acids and such salts are included in the present invention.

This invention also includes the use of the compounds of Formula (A) in the treatment and prevention of neoplasms, particularly of the uterus, ovary and breast, and in the treatment and prevention of menopausal disorders and osteoporosis. The invention further includes pharmaceutical compositions comprising one or more of the compounds of Formula (A) and one or more pharmaceutically acceptable excipients.

In vitro results have shown that the compound of the invention have a marked affinity to type II estrogen receptors and are inhibitors of tyrosine kinase. Further they are capable of inhibiting the activity of the P-170 protein pump that mediates the MDR in tumoral cells, and of antagonizing the proliferation of both hormone-dependent and chemoresistant tumoral cells in the same proportion.

The mechanisms of action of the compounds of Formula (A) are most probably different from the those of structurally related prior art compounds, (including natural occurring chalcones) inasmuch as they can completely inhibit protein P-170. For these reasons, the compounds of the invention show a more marked activity, both in vitro and in vivo, than other products known in the prior art.

The affinity of some compounds for type II receptors and the antiproliferative activity on ovarian tumoral cells are shown in Table 1.

TABLE 1

Affinity for type II estrogen receptors and antiproliferation activity in vitro on a sensitive, MDA, adriamycin-resistant, MCF-7ADR, human breast tumoral line.

| Compounds | $IC_{50}$ * μM (MDA-MB231) | $IC_{50}$ * μM (MCF7 ADRr) | $IC_{50}$ ** μM |
|---|---|---|---|
| I | 3.2 | 2.8 | 1.1 |
| II | 3.2 | 2.2 | 3.3 |
| III | 8.2 | 7.0 | 4.2 |

TABLE 1-continued

Affinity for type II estrogen receptors and antiproliferation activity in vitro on a sensitive, MDA, adriamycin-resistant, MCF-7ADR, human breast tumoral line.

| Compounds | $IC_{50}$ * $\mu M$ (MDA-MB231) | $IC_{50}$ * $\mu M$ (MCF7 ADRr) | $IC_{50}$ ** $\mu M$ |
|---|---|---|---|
| IV | 7.5 | 9.4 | 1.7 |
| V | 11.0 | 6.8 | 2.8 |
| VI | 9.6 | 8.8 | 3.4 |
| VII | 7.1 | 9.4 | 5.2 |
| VIII | 5.4 | 6.0 | 4.0 |
| IX | 5.0 | 8.9 | 3.1 |
| X | 3.7 | 3.7 | 2.8 |

\* concentration causing 50% inhibition of the cell proliferation
\*\* concentration causing 50% displacement of the estradiol labelled by its own receptor.

The binding to type II estrogen receptors was evaluated in ovarian tumor cells and tumor cells of other target organs. The cells were grown in a single layer according to the known techniques reported in the literature. To make the test reproducibility, the cells were trypsin treated, every week and placed on plates at a density of $8 \times 10^4$ cells/cm$^2$ and incubated at 37° C. in air containing 5% $CO_2$.

The various compounds under test, dissolved in ethyl alcohol, were added at serial dilutions and the treated cells and control cells were incubated with $^3$H-estradiol or in the presence of diethylstilbestrol according to the methods described by literature. The antiproliferation activity were verified in the same way by adding the compounds, dissolved in DMSO, to the medium and performing a cell count after 72 hours.

The compounds according to this invention inhibit the cell proliferation in vivo as can be demonstrated by examining the size of the tumours implanted in athymic naked mice according to the techniques that are extensively reported in literature.

Treatment of animals with doses ranging from 1 mg/kg to 200 mg/kg produced a marked reduction in size of the tumours with the total retrogression of the tumour in many of the animals treated.

The compounds according to the invention can suitably be administered enterally or parenterally (e.g. orally or by injection) in pharmaceutically acceptable vehicles. The dosage for treatment and prevention of neoplasms with the compounds of the invention (which are essentially non-toxic) can vary from 50 mg to 1,000 mg per day for a time ranging from a month to several years depending on the nature and severity of the disease.

The compounds of the invention are especially useful in combination therapies along with other anti-neoplastic drugs and/or physical anti-cancer treatments such as radiotherapy. Thus, for example, they can advantageously be administered in anti-tumor therapy prior to treatment with antiblastic drugs, so that the dosage of the latter and, consequently, their unwanted side effects, can be reduced to the patient's advantage.

Given their clear antiproliferation activity on hormone-dependent tumoral cells and the activity on protein kinase, treatment of patients can be continued after the traditional chemotherapy or surgical operation for the removal of the tumour in order to block metastatic diffusion. The same compounds according to this invention can be used in prophylactic treatment for the prevention of tumours in the uterus, ovary and breast, as well as for the reduction of typical menopausal disorders.

In such cases the dosage may range from 5 mg/kg up to 100 mg/kg per day and furthermore the products may advantageously be administered orally in formulations containing phospholipids which facilitate their resorption.

The compounds according to the invention can be synthesized in two main ways:
a) by the reaction between an equimolar solution of acetophenone and an appropriate aldehyde in ethyl alcohol in the presence of KOH; and
b) by reacting an equimolar solution of acetophenone and an appropriate aldehyde in ethyl alcohol in the presence of piperidine and acetic acid under weak countercurrent.

At the end of the reaction, the products may crystallized from alcoholic solution or purified by means of chromatography. The reaction products generally have a high degree of purity, so that crystallization is usually sufficient to obtain the desired products in a high degree of purity.

The following examples illustrate the invention more in detail without limiting it.

EXAMPLES

Example I

General Conditions to Obtain Chalcones.
Method A.
A solution of KOH 50% is added to an equimolar solution of acetophenone (0.075 mol) and aldehyde (0.075 mol) in ethanol 95%; the addition is performed under energetic stirring at room temperature. The reaction is left under stirring for one night and then diluted with water and acidified; the precipitate is separated by filtration and dried under vacuum. The compounds are crystallized by ethanol or first separated by chromatography and then crystallized by ethanol.
Method B.
A solution of acetophenone (0.075 mol), aldehyde (0.075 mol), piperidine (15 ml) and acetic acid (75 ml) in ethyl alcohol 95% (80 ml) is countercurrent heated for 5 hours. Molecular sieves are added to the solution to eliminate water and the whole is left at rest for one night. The precipitate that is generally obtained is gathered and crystallized. If the product does not precipitate in these conditions, the solvent is vacuum evaporated and the residue is purified by chromatography on a silica gel column.

Example II

Preparation of 1-[2-hydroxy-4-(3-methylbut-2-enyloxy)-phenyl]-3(pyridine-4-yl)-propen-1-one; Compound I A solution of KOH 50% (3 ml) is added in drops, under stirring, to a solution containing 2.2 gm (10 mmol) 2-hydroxy4-(3-methylbut-2-enyloxy)-acetophenone and 1.07 gm (10 mmol) pyridine-4-carboxyaldehyde in 25 ml ethanol 95%. The solution is kept under stirring for one night at room temperature and then poured in 60 ml water. It is then acidified with diluted HCl and then filtered; the residue is crystallized twice by ethanol 95%. This yields 1.9 gm of a product with the following characteristics: m.p. 99–100° C.; $^1$H NMR $\delta$(CHCl$_3$): 1.68 (s, 3H, CH$_3$), 1.7 (s, 3H, CH$_3$), 4.53 (d, 2H, OCH$_2$), 5.45 (m, 1H, CH=), 6.5–6.7 (m, 2H, olefins), 8.7–9.1 (m, 7H, Ar). Mass: M/z (%): 309 (M$^+$, 7.57), 241 (59.12), 163 (62.41), 69 (100).

Example III

Preparation of 1-[2-hydroxy-4-(3-methylbut-2-enyloxy)-phenyl]-3(pyridine-3-yl)-propen-1-one; Compound II A solution of KOH 50% (3 ml) is added in drops, under stirring, to a solution containing 2.2 gm (10 mmol)

2-hydroxy-4-(3-methylbut-2-enyloxy)-acetophenone and 1.07 gm (10 mmol) pyridine-3-carboxyaldehyde in 25 ml ethanol 95%. The solution is kept under stirring for one night at room temperature and then poured in 60 ml water. It is then acidified with diluted HCl and then filtered; the residue is crystallized twice by ethanol 95%. This yields 1.6 gm of a product with the following characteristics: m.p. 177–79° C.; $^1$H NMR δ(CHCl$_3$): 1.65 (s, 3H, CH$_3$), 1.72 (s, 3H, CH$_3$), 4.64 (d, 2H, OCH$_2$), 5.42 (m, 1H, CH=), 6.5–6.65 (m, 2H, olefins), 7.8–9.4 (m, 7H, Ar). Mass: M/z (%): 309 (M$^+$, 10.76), 241 (71.17), 163 (43.17), 69 (100).

Example IV

Preparation of 1-[2-hydroxy-4-(3-methylbut-2-enyloxy)-phenyl]-3-(4-acetamide)-phenyl-propen-1-one; Compound III A solution of KOH 50% (3 ml) is added in drops, under stirring, to a solution containing 2.2 gm (10 mmol) 2-hydroxy-4-(3-methylbut-2-enyloxy)-acetophenone and 1.63 gm (10 mmol) 4-acetamide benzaldehyde in 25 ml ethanol 95%. The solution is kept under stirring for one night at room temperature and then poured in 60 ml water. It is then acidified with diluted HCl and extracted with methylene chloride. The organic solution is washed with water, desiccated and dry evaporated. The residue is purified by chromatography on a silica gel column while eluting with a mixture of toluene/ethyl acetate in a ratio of 9:1. After collecting the staring acetophenone (30%), elute the product required having the following characteristics: m.p. 150–152° C.; $^1$H NMR δ (CHCl$_3$):1.75 (s, 3H, CH$_3$), 1.8 (s, 3H, CH$_3$), 2.2 (s, 3H, COCH$_3$), 4.55 (d, 2H, OCH$_2$), 5.6 (m, 1H, CH=), 6.4–6.5 (m, 2H, olefins), 7.3 (broad, 1H, NH), 7.4–7.9 (m, 7H, Ar). Mass: m/z (%): 365 (M$^+$, 48.38), 297 (100), 148 (70.77), 69 (97.15).

Example V

Preparation of 1-[2-hydroxy-4-(2-methylallyloxy)-phenyl-3-(4-dimethylamine)-phenyl]-propen-1-one, Compound IV A solution containing 2.06 gm (10 mmol) 2-hydroxy-4-(2-methylallyloxy)acetophenone, 1.79 gm (10 mmol) 4-dimethylaminebenzaldehyde, 11 ml ethanol 95%, 2 ml piperidine and 15 ml glacial acetic acid is countercurrent heated for 5 hours. After the addition of molecular sieves, the solution is left at rest for one night; it is then filtered and the precipitate is crystallized by ethanol 95%. This yields 0.75 gm of a product with the following characteristics: m.p. 85–87° C.; $^1$H NMR δ (CHCl$_3$): 1.85 (s, 3H, CH$_3$), 3.02 (s, 6H, NMe,), 4.48 (s, 2H, CH$_2$=), 5.05 (d, 2H, OCH$_2$), 6.4–6.5 (m, 2H, olefins), 6.6–7.9 (m, 7H, Ar). Mass: m/z (%): 337 (M$^+$, 55.97), 147 (100), 134 (67.67), 55 (8.87).

Example VI

Preparation of 1-[2-hydroxy-4-(3-methylbut-2-enyloxy)-phenyl-3-(indole-3-yl)-propen-1-one; Compound V A solution containing 2.2 gm (10 mmol) 2-hydroxy-4-(2-enyloxy)-acetophenone, 1.45 gm (10 mmol) indole-3-carboxyaldehyde, 11 ml ethanol 95%, 2 ml piperidine and 15 ml glacial acetic acid is countercurrent heated for 5 hours. After the addition of molecular sifts, the solution is left at rest for one night; it is then dry evaporated and subjected to chromatography on a silica gel column while eluting with petroleum ether/ethyl acetate in a ratio of 3:7. After eliminating the starting acetophenone, gather 0.8 gm of the product required having the following characteristics: m.p. 228–230° C. (Toluene); $^1$H NMR δ (DMSO): 1.72 (s, 3H, CH$_3$), 1.76 (s, 3H, CH$_3$), 4.64 (d, 2H, OCH$_2$), 5.45 (t, 1H, CH=), 6.5–6.6 (m, 2H, olefins), 7.2–8.2 (m, 8H, Ar), 12 (s, 1H, OH). Mass: m/z (%): 347 (M$^+$, 55.88), 143 (100), 130 (85.83), 69 (40.80).

Example VII

Preparation of 1-[2-hydroxy-4-(2-methylallyloxy)-phenyl]-3-(indole-3-yl)-propen-1-one; Compound VI A solution containing 2.06 gm (10 mmol) 2-hydroxy-4-(2-methylallyloxy)acetophenone, 1.45 gm (10 mmol) indole-3-carboxyaldehyde, 11 ml ethanol 95%, 2 ml piperidine and 15 ml glacial acetic acid is countercurrent heated for 5 hours. After the addition of molecular sifts, the solution is left at rest for one night; it is then dry evaporated and subjected to chromatography on a silica gel column while eluting with petroleum ether/ethyl acetate in a ratio of 3:1. After eliminating the starting acetophenone, gather 0.7 gm of the product required having the following characteristics: m.p. 29–30° C.; $^1$H NMR δ (CHCl$_3$): 1.8 (s, 3H, CH$_3$), 4.55 (s, 2H, CH$_2$=), 5.05 (d, 2H, OCH$_2$) 6.4–6.5 (m, 2H, olefins), 7.4–7.9 (m, 8H, Ar). Mass: m/z (%): 333 (M$^+$, 44.03), 143 (100), 130 (48.23), 115 (17.10).

Example VIII

Preparation of 1-[2-hydroxy-4-(prop-2-enyloxy)-phenyl-3-(indole-3-yl)propyn-1-one, compound VII A solution containing 1.9 gm (10 mmol) 2-hydroxy-4-(prop-2-ynyloxy)-acetophenone, 1.45 gm (10 mmol) indole-3-carboxyaldehyde, 11 ml ethanol 95%, 2 ml piperidine and 15 ml glacial acetic acid is countercurrent heated for 5 hours. After the addition of molecular sifts, the solution is left at rest for one night; it is then dry evaporated and subjected to chromatography on a silica gel column while eluting with petroleum ether/ethyl acetate in a ratio of 3:1. After eliminating the starting acetophenone, gather 0.8 gm of the product required having the following characteristics: m.p. 228–230° C.; $^1$H NMR δ(CHCl$_3$): 2.5 (t, I H, CH=), 4.65 (s, 2H, OCH$_2$), 6.4–6.5 (m, 2H, olefins), 7.1–8.2 (m, 9H, Ar and NH), 11 (broad, 1 H, OH). Mass: m/z (%): 317 (M', 27.02), 143 (50.70),130 (23.40), 91 (41.09).

Example IX

Preparation of 1-[2-hydroxy-4-(2-methylallyloxy)-phenyl]-3-(pyridine-3-yl)-propen-1-one, compound VIII A solution of KOH 50% (3 ml) is added in drops, under stirring, to a solution containing 2.06 gm (10 mmol) 2-hydroxy-4-(2-methylallyloxy)-acetophenone and 1.07 gm (10 mmol) pyridine-3-carboxyaldehyde in 25 ml ethanol 95%. The solution is kept under stirring for one night at room temperature and then poured in 60 ml water. It is then acidified with diluted HCl and-then filtered; the residue is crystallized by ethanol 95%. This yields 1.4 gm of a product with the following characteristics: m.p. 164–166° C.; $^1$H NMR δ (CHCl$_3$): 1.8 (s, 3H, CH$_3$), 4.5 (s, 2H, CH$_2$=),5.8 (d, 2H, OCH$_2$), 6.4–6.6 (m,2H, olefins), 7.3–8.9 (m, 7H, Ar). Mass: m/z (%): 295 (M$^+$, 45.98), 240 (21.93), 217 (35.55), 132 (24.23), 55 (100).

Example X

Preparation of 1-[2-hydroxy-4-(3-methylallyloxy)-phenyl-3-(3-methoxyphenyl)-propen-1-one; Compound IX A solution of KOH 50% (3 ml) is added in drops, under stirring, to a solution containing 2.06 gm (10 mmol) 2-hydroxy-4-(3-methylallyloxy)-acetophenone and 1.36 gm (10 mmol) 3-methoxybenzaldehyde in 25 ml ethanol 95%. The solution is kept under stirring for one night at room temperature and then poured in 60 ml water. It is then acidified with diluted HCl and then filtered; the residue is crystallized by ethanol 95%. This yields 1.7 gm of a product with the following characteristics: m.p. 97–100° C.; $^1$H NMR δ (CHCl$_3$):2.54 (t, 1H, CH=), 3.82 (s, 3H, OCH$_3$), 4.70 (s, 2H, OCH$_2$), 6.5–6.6 (m, 2H, olefins), 6.9–7.9 (m, 7H, Ar). Mass: m/z (%): 308 (M$^+$, 100), 269 (19.75), 161 (56.42), 134 (65.79), 118 (32.73).

Example XI

Preparation of 1-[2-hydroxy-4-(prop-2-enyloxy)-phenyl-3-(pyridine-3-yl)propen-1-one, compound X A solution of KOH 50% (3 ml) is added in drops, under stirring, to a solution containing 1.9 gm (10 mmol) 2-hydroxy-4-(prop-2-enyloxy)-acetophenone and 1.07 gm (10 mmol) pyridine-3-carboxyaldehyde in 25 ml ethanol 95%. The solution is kept under stirring for one night at room temperature and then poured in 60 ml water. It is then acidified with diluted HCl and then filtered; the residue is crystallized by ethanol 95%. This yields 1.5 gm of a product with the following characteristics: m.p. 115–117° C.; $^1$H NMR δ (CHCl$_3$): 2.5 (t, 1H, CH=), 4.8 (s, 2H, OCH$_2$), 6.55–6.65 (m, 2H, olefins), 7.3–8.9 (m, 7H, Ar). Mass: m/z (%): 279 (M$^+$, 100), 240 (27.47), 201 (74.86), 147 (24.90), 104 (49.93).

What is claimed is:

1. A compound of formula (A)

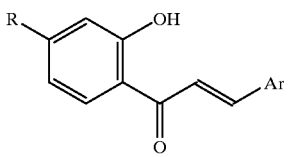

(A)

wherein

Ar represents 3-pyridyl; 4-pyridyl; or 3-indolyl; and

R represents —OCH$_2$R$_1$, in which R$_1$ is selected from —CH=CMe$_2$, —CMe=CH$_2$, or —C≡CH.

2. A compound selected from the group consisting of:
   1-[2-hydroxy-4-(3-methylbut-2-enyloxy)-phenyl]-3-(pyridine-4-yl)-propen-1-one,
   1-[2-hydroxy-4-(3-methylbut-2-enyloxy)-phenyl]-3-(pyridine-3-yl)-propen-1-one,
   1-[2-hydroxy-4-(3-methylbut-2-enyloxy)-phenyl]-3-(indole-3-yl)-propen-1-one,
   1-[2-hydroxy-4-(2-methylallyloxy)-phenyl]-3-(indole-3-yl)-propen-1-one,
   1-[2-hydroxy-4-(prop-2-ynyloxy)-phenyl]-3-(pyridine-3-yl)-propen-1-one,
   1-[2-hydroxy-4-(2-methylallyloxy)-phenyl]-3-(indole-3-yl)-propen-1-one,
   1-[2-hydroxy-4-(prop-2-ynyloxy)-phenyl]-3-(pyridine-3-yl)-propen-1-one.

3. A pharmaceutical composition comprising a compound of formula (A)

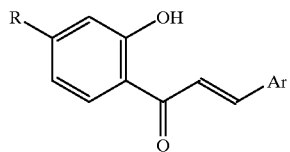

(A)

and a pharmaceutically acceptable excepient, wherein, in formula (A),

Ar represents 3-pyridyl; 4-pyridyl; or 3-indolyl; and

R represents —OCH$_2$R$_1$, in which R$_1$ is selected from —CH=CMe$_2$, —CMe=CH$_2$, or —C≡CH.

4. A pharmaceutical composition comprising a pharmaceutically acceptable excipient and a compound selected from the group consisting of:
   1-[2-hydroxy-4-(3-methylbut-2-enyloxy)-phenyl]-3-(pyridine-4-yl)-propen-1-one,
   1-[2-hydroxy-4-(3-methylbut-2-enyloxy)-phenyl]-3-(pyridine-3-yl)-propen-1-one,
   1-[2-hydroxy-4-(3-methylbut-2-enyloxy)-phenyl]-3-(indole-3-yl)-propen-1-one,
   1-[2-hydroxy-4-(2-methylallyloxy)-phenyl]-3-(indole-3-yl)-propen-1-one,
   1-[2-hydroxy-4-(prop-2-ynyloxy)-phenyl]-3-(indole-3-yl)-propen-1-one,
   1-[2-hydroxy-4-(2-methylallyloxy)-phenyl]-3-(pyridine-3-yl)-propen-1-one, and
   1-[2-hydroxy-4-(prop-2-ynyloxy)-phenyl]-3-(pyridine-3-yl)-propen-1-one.

5. A method for treating or preventing neoplasms, menopausal disorders, and osteoporosis in a mammal, which comprises administering to the mammal a therapeutically effective amount of a compound of formula (A)

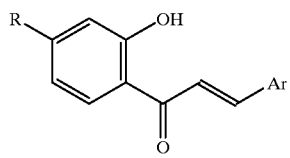

(A)

wherein, in formula (A),

Ar represents 3-pyridyl; 4-pyridyl; or 3-indolyl; and

R represents —OCH$_2$R$_1$, in which R$_1$ is selected from —CH=CMe$_2$, —CMe=CH$_2$, or —C≡CH.

6. The method of claim 5, wherein the compound to be administered is selected from the group consisting of:
   1-[2-hydroxy-4-(3-methylbut-2-enyloxy)-phenyl]-3-(pyridine-4-yl)-propen-1-one,
   1-[2-hydroxy-4-(3-methylbut-2-enyloxy)-phenyl]-3-(pyridine-3-yl)-propen-1-one,
   1-[2-hydroxy-4-(3-methylbut-2-enyloxy)-phenyl]-3-(indole-3-yl)-propen-1-one,
   1-[2-hydroxy-4-(2-methylallyloxy)-phenyl]-3-(pyridine-3-yl)-propen-1-one,
   1-[2-hydroxy-4-(prop-2-ynyloxy)-phenyl]-3-(indole-3-yl)-propen-1-one,
   1-[2-hydroxy-4-(2-methylallyloxy)-phenyl]-3-(indole-3-yl)-propen-1-one, and 1-[2-hydroxy-4-(prop-2-ynyloxy)-phenyl]-3-(pyridine-3-yl)-propen-1-one.

7. The method of claim 5, wherein the neoplasm is of the uterus, ovary, or breast.

8. The method of claim 5, wherein the compound is present with a pharmaceutically acceptable vehicle and is administered orally or by injection.

9. The method of claim 5, wherein the amount of the compound administered ranges from about 1 mg/kg to about 200 mg/kg.

10. The method of claim 5, wherein the method is for treating or preventing neoplasms and the amount of the compound administered ranges from about 50 mg to about 1000 mg per day for a time ranging from about a month to several years.

11. The method of claim 5, wherein the compound is administered for prophylactically preventing tumors in the uterus, ovary, and breast or for treating menopausal disorders and the amount of the compound administered ranges from about 5 mg/kg to about 100 mg/kg per day.

12. A process for synthesizing a compound of formula (A)

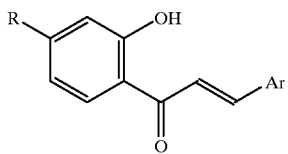

(A)

wherein
Ar represents 3-pyridyl; 4-pyridyl; or 3-indolyl; and
R represents —OCH$_2$R$_1$, in which R$_1$ is selected from —CH=CMe$_2$, —CMe=CH$_2$, or —C≡CH;
said process comprises
(1) reacting equimolar solution of acetophenone and an aldehyde in ethyl alcohol in the presence of KOH; or
(2) reacting equimolar solution of acetophenone and an aldehyde in ethyl alcohol in the presence of piperidine and acetic acid under weak countercurrent.

13. The process of claim 12, further comprising crystallizing the reaction product from the alcoholic solution or purifying the reaction product by means of chromatography.

* * * * *

UNITED STATES PATENT AND TRADEMARK OFFICE
CERTIFICATE OF CORRECTION

PATENT NO. : 6,147,082
DATED : November 14, 2000
INVENTOR(S) : Bombardelli et al.

It is certified that error appears in the above-identified patent and that said Letters Patent is hereby corrected as shown below:

ON THE TITLE PAGE
Please Add:
--Item [73] Assignee: Indena S.p.A., Milano, Italy --.

INID code "[76]" should read -- [75] --.

Signed and Sealed this

Nineteenth Day of June, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,147,082
DATED        : November 14, 2000
INVENTOR(S)  : Ezio Bombardelli et al.

Page 1 of 1

It is certified that error appears in the above-identified patent and that said Letters Patent is hereby corrected as shown below:

Column 7,
Line 62, change "(pyridine-3-" to -- (indole-3- --.
Line 64, change "(indole-3-" to -- (pyridine-3- --.

Column 8,
Line 62, change "(pyridine-" to -- (indole- --.
Line 66, change "(indole-3-" to -- pyridine-3- --.

Signed and Sealed this

Eighteenth Day of March, 2003

JAMES E. ROGAN
*Director of the United States Patent and Trademark Office*